United States Patent [19]
Shanbrom et al.

[11] Patent Number: 6,096,216
[45] Date of Patent: Aug. 1, 2000

[54] IODINATED MATRICES FOR DISINFECTING BIOLOGICAL FLUIDS

[75] Inventors: Edward Shanbrom, 2252 Liane La., Santa Ana, Calif. 92705; Shirley I. Miekka, Gaithersburg, Md.; Robert Pollock, Arlington; William N. Drohan, Springfield, both of Va.; Timothy W. Horton, Martinsville, N.J.

[73] Assignees: American National Red Cross, Falls Church, Va.; Amersham Pharmacia Biotech, Inc., Sweden; Edward Shanbrom, Santa Ana, Calif.

[21] Appl. No.: 08/813,337

[22] Filed: Mar. 7, 1997

Related U.S. Application Data

[63] Continuation-in-part of application No. 08/667,448, Jun. 21, 1996, Pat. No. 5,814,225, which is a continuation-in-part of application No. 08/562,795, Nov. 27, 1995, abandoned, which is a continuation of application No. 08/255,616, Jun. 9, 1994, abandoned.

[51] Int. Cl.⁷ .................................................. B01D 15/04
[52] U.S. Cl. .......................... 210/638; 210/651; 210/645; 210/656; 210/198.2; 210/502.1; 424/78.1
[58] Field of Search ...................................... 210/651, 645, 210/638, 656, 198.2, 301, 502.1, 658, 753; 424/78.1, 667

[56] References Cited

U.S. PATENT DOCUMENTS

| | | |
|---|---|---|
| 3,401,005 | 9/1968 | Katz . |
| 3,817,860 | 6/1974 | Lambert et al. . |
| 4,010,259 | 3/1977 | Johansson . |
| 4,076,622 | 2/1978 | Costin . |
| 4,187,183 | 2/1980 | Hatch . |
| 4,238,477 | 12/1980 | Lambert et al. . |
| 4,381,380 | 4/1983 | LeVeen et al. . |
| 4,396,608 | 8/1983 | Tenold . |
| 4,420,590 | 12/1983 | Gartner . |
| 4,460,642 | 7/1984 | Errede ..................................... 428/283 |
| 4,499,073 | 2/1985 | Tenold . |
| 4,594,392 | 6/1986 | Hatch . |
| 4,883,587 | 11/1989 | LeVeen et al. . |
| 4,888,118 | 12/1989 | Barnes et al. . |
| 4,915,839 | 4/1990 | Marinaccio et al. . |
| 4,946,673 | 8/1990 | Pollack ..................................... 424/667 |
| 4,999,190 | 3/1991 | Fina et al. . |
| 5,071,648 | 12/1991 | Rosenblatt . |
| 5,137,718 | 8/1992 | Gillespie . |
| 5,176,836 | 1/1993 | Sauer et al. . |
| 5,302,392 | 4/1994 | Karakelle et al. . |
| 5,326,841 | 7/1994 | Fellman . |
| 5,360,605 | 11/1994 | Shanbrom . |
| 5,370,869 | 12/1994 | Shanbrom . |
| 5,431,908 | 7/1995 | Lund . |
| 5,545,401 | 8/1996 | Shanbrom . |
| 5,589,072 | 12/1996 | Shanbrom . |
| 5,591,350 | 1/1997 | Piechocki et al. . |
| 5,609,864 | 3/1997 | Shanbrom . |
| 5,624,567 | 1/1997 | Colombo ................................. 210/683 |
| 5,639,452 | 6/1997 | Messier ................................. 424/78.1 |

FOREIGN PATENT DOCUMENTS

| | | |
|---|---|---|
| WO85/02422 | 6/1985 | WIPO . |
| WO92/04031 | 3/1992 | WIPO . |
| WO92/04061 | 3/1992 | WIPO . |
| WO93/04678 | 3/1993 | WIPO . |
| WO93/04730 | 3/1993 | WIPO . |
| WO93/04731 | 3/1993 | WIPO . |
| WO93/06911 | 4/1993 | WIPO . |
| WO93/17693 | 9/1993 | WIPO . |
| WO93/21933 | 11/1993 | WIPO . |
| WO93/25268 | 12/1993 | WIPO . |
| WO94/00011 | 1/1994 | WIPO . |
| WO94/06289 | 3/1994 | WIPO . |
| 96/20019 | 7/1996 | WIPO . |
| WO97/48422 | of 1997 | WIPO . |
| WO97/48482 | of 1997 | WIPO . |

OTHER PUBLICATIONS

L.E. Osterhoudt, "Iodinated resin and its use in water disinfection" *Say You Saw It In Filtration News* May/Jun. 1996 Issue p. 22.

Miekka et al, "New Methods for Inactivation of Lipid–Enveloped and Non–Enveloped Viruses", *Haemophilia*, vol. 4, pp. 402–408 (1998).

Gottardi, W., "Iodine and Iodine Compounds in Disinfection, Sterilization, and Preservation", (Block, Seymour S., Ed.) Lea & Febiger, Philadelphia (3d ed., 1983).

*Primary Examiner*—Ana Fortuna
*Attorney, Agent, or Firm*—Burns, Doane, Swecker & Mathis, L.L.P.

[57] ABSTRACT

The present invention provides media for inactivating pathogens found within protein-containing biological fluids. The media of the present invention preserve the structural integrity and biological activity of labile proteins while simultaneously exhibiting potent disinfectant activity. The media of the present invention comprise iodinated chromatographic media, particularly ion exchange media. The invention further provides methods for disinfecting biological fluids.

52 Claims, No Drawings

IODINATED MATRICES FOR DISINFECTING BIOLOGICAL FLUIDS

CROSS REFERENCE TO RELATED APPLICATIONS

This is a continuation in part application of U.S. patent application Ser. No. 08/667,448, filed Jun. 21, 1996, U.S. Pat. No. 5,814,225, which is a continuation in part application of U.S. patent application Ser. No. 08/562,795, filed Nov. 27, 1995, abandoned, which is a continuation of U.S. patent application Ser. No. 08/255,616, filed Jun. 9, 1994, abandoned.

FIELD OF THE INVENTION

The present invention provides matrices for disinfecting biological fluids such as blood, blood fractions, and blood products. The matrices of the present invention are of particular advantage in disinfecting mixtures containing labile proteins. The matrices of the present invention comprise iodinated chromatography media, particularly ion exchange media. The invention further provides methods for disinfecting biological fluids.

BACKGROUND OF THE INVENTION

The use of iodine as an aerial disinfectant has been advocated at least since 1926, and experiments on the disinfection of air have been carried out, mainly during World War II. Aerial disinfection of air-raid shelters with iodine vapors as a prophylactic measure against influenza has been recommended. A "relatively tolerable" concentration of 0.1 mg/ft$^3$ (3.5 ng/ml) was found to be sufficient for a rapid kill of freshly sprayed salivary organisms.

Although it is a strong skin irritant, iodine can be used effectively in medicine as a disinfectant when combined with suitable carriers or complexing agents, e.g., an iodophor. For example, complexed or "tamed iodine" is used in medicine in disinfecting skin (e.g., preoperative preparation of the skin, the surgical disinfection of hands, the disinfection of the perineum prior to delivery, and disinfection of skin prior to transfusions). Iodine preparations are also used for therapeutic purposes, e.g. the treatment of infected and burned skin. Iodine has also been used for the disinfection of medical equipment, such as catgut, catheters, knife blades, ampoules, plastic items, rubber goods, brushes, multiple-dose vials, and thermometers.

Iodine is also known to be useful in disinfecting drinking water. Iodine can inactivate viruses more completely over a wide range of water quality than other halogens. In the presence of organic and inorganic nitrogenous substances, iodine is the cytocide of choice because it takes part in fewer side reactions that consume the disinfectant before it can act. See, e.g., Gottardi, W., *Iodine and Iodine Compounds in Disinfection, Sterilization, and Preservation,* (Block, Seymour S., Ed.) Lea & Febiger, Philadelphia (3d ed. 1983) and references cited therein.

Johansson, U.S. Pat. No. 4,010,259, described methods and materials for complexing iodine with various iodophors. The iodophors of the '259 patent are described as those in which the iodine is non-covalently bonded to a hydrophilic organic carrier. The organic carrier is insoluble in water, but capable of swelling in water to form a gel. The media of the '259 patent have low capacity for iodine uptake, and iodination occurs slowly. To offset those shortcomings, the '259 patent teaches that iodination is best effected at elevated temperatures.

More recently, Shanbrom reported that suitably constituted iodophors can be used with some success to disinfect platelet-bearing fluid. See, e.g., Shanbrom, E., U.S. Pat. No. 5,360,605, "Preservation of Blood, Tissues and Biological Fluids", which is a continuation in part of the patent application that matured into U.S. Pat No. 5,370,869, "Antimicrobial Preservation of Platelets and Blood Factors", both of which are incorporated herein by reference. Those patents teach that iodine complexed with polyvinyl pyrrolidone ("PVP", e.g., povidone USP), is an effective iodophor for killing or inactivating certain pathogens in biological fluids, particularly platelet-bearing fluid.

The '869 patent teaches that disinfecting agents such as $I_2$ and hydrogen peroxide ($H_2O_2$) can be effectively complexed with polyvinyl pyrrolidone (e.g., povidone USP); and that such PVP complexes can be used to disinfect platelet-containing fluids. The '869 patent teaches that the disclosed PVP disinfecting agents must utilize low molecular weight PVP (povidones), i.e., under 40,000 daltons, preferably under 20,000 daltons. According to the '869 patent, low molecular weight PVP is necessary to avoid the destruction of cells and various blood factors normally occasioned by treatment with iodine.

The '869 patent describes compounding the iodine-complexed low molecular weight povidone into a solution containing 0.1–10% (by weight) povidone. The '869 patent teaches that povidone-$I_2$ is constituted such that the ratio of povidone to $I_2$ (povidone:$I_2$) is at least about 12:1, preferably in the range of 15:1 to 60:1. The '869 patent states that such povidone-,$I_2$ solutions are effective for disinfecting platelet-bearing fluids, and, presumably, for enhancing the storage stability of such fluids.

The related '605 patent teaches that PVP is a particularly advantageous iodine carrier in that it protects cells against lytic agents such as iodine (i.e., exerts a cytophylactic effect); and that to maintain a cytophylactic effect a PVP:$I_2$ ratio of at least about 15:1 must be maintained. Even so, the '605 patent teaches that it is still necessary to remove residual iodine from biological fluids treated with povidone-$I_2$ to avoid the destruction of labile proteins. The '605 patent teaches that this can be effected by removing the iodine (e.g., by adding a competitive iodine-binding material), or by neutralizing the iodine (e.g., by adding a reducing agent such as ascorbic acid, reducing sugars, sodium sulfite, etc.).

Furthermore, povidone is water-soluble and is technically difficult to remove from treated fluids. Crosslinked PVP (XLPVP) an insoluble form of povidone, can also be used as a carrier for iodine (XLPVPI) and is more readily removed from the treated fluid by filtration or centrifugation. However, the flow properties of XLPVPI are poor. Therefore, it is not feasible to use this material in a column or depth filter mode, in which fluids would be passed through a packed bed of the material as needed from large volume processing in a manufacturing-scale setting.

Despite the foregoing, the art has failed to produce an effective, reliable, and commercially practical means for achieving satisfactory levels of disinfection of biological fluids without concomitant destruction of labile proteins. For example, workers have long since struggled to achieve inactivation of viruses that do not possess a lipid envelope (i.e., "non-lipid-enveloped viruses") and similarly hardy pathogens such as viral-elements (e.g., prions). Current methods (e.g., solvent and detergent treatment, methylene blue plus light treatment), inactivate viruses possessing a lipid envelope (i.e., "lipid-enveloped viruses"), but have little or no effect on non-lipid-enveloped viruses or prions.

Furthermore, known methods utilizing iodine inactivation fail to effectively control the release of iodine and the duration of exposure of the proteins, and thereby tend to denature proteins.

The methods of the present invention afford a controlled release of iodine into biological fluids so as to achieve selective inactivation of pathogens, especially non-lipid enveloped viruses and viral elements, without simultaneous inactivation or denaturation of valuable but labile proteins in biological fluids. The methods of the present invention afford viral inactivation of biological fluids on a greater scale than that heretofore available.

OBJECTS AND SUMMARY OF THE INVENTION

It is an object of the present invention to provide materials and methods for disinfecting biological fluids such as blood, blood fractions and other protein-containing solutions and mixtures;

It is an additional object of the present invention to provide a reliable, storage stable, commercially available material effective for disinfecting biological fluids; and It is a further object of the present invention to provide a reliable, storage stable, commercially available material that can disinfect biological fluids without destroying or damaging the biologically and therapeutically significant components therein.

These and other objects of the present invention are fulfilled by the methods and materials disclosed herein.

DETAILED DESCRIPTION OF THE PREFERRED EMBODIMENTS

The following description will enable a person skilled in the art to which this invention pertains to make and use the invention, and sets forth the best modes contemplated by the inventors of carrying out their invention.

The present invention provides materials and methods useful in disinfecting biological fluids, particularly blood, blood fractions, blood plasma and plasma derived products, as well as fluids associated with the production of recombinant and transgenic products, e.g., cell culture supernatants, milk, etc.

Materials useful in the present invention include insoluble matrix materials complexed with a disinfecting agent such as a halogen, hydrogen peroxide, or other oxidizing or derivatizing agent. Preferred materials include iodinated chromatographic matrix materials. Particularly preferred matrix materials are iodinated ion exchange resins.

As used herein, and unless stated otherwise, the term "iodine" (or "iodinated") includes iodine in any of its various forms, e.g., diatomic iodine ($I_2$), ionic iodine (e.g., $I^-$ or iodide), iodine as free radical, molecular ionic iodine (e.g., triiodide anion ($I_3^-$)), and related species derived from $I_2$.

the term "blood products" includes blood fractions such as plasma and blood derived products such as clotting factors, red cell platelets, white cells, immunoglobulins and the like;

the term "biological fluid" refers to a protein-containing fluid of human or non-human origin, whether solution, mixture or suspension, and includes blood, blood fractions, milk, urine, semen, saliva, cell culture supernatants, and other fluids, of either natural or synthetic origin, that contain biologically significant components, particularly proteins;

the term "matrix material" refers to any insoluble, durable material conventionally used as a carrier or substrate material in a chemical separations process and capable of complexing, adsorbing, or otherwise binding iodine; and the term "disinfect" means to inactivate, kill, or otherwise render non-pathogenic a pathogenic contaminant found in blood such as a virus, bacterium, microorganism, or other pathogenic species such as a prion, prion-related protein ("PRP"), etc.

Unless stated otherwise, all quantities or concentrations expressed as a percentage (%) are percent by weight.

Preferred Media and Methods of Application

The present invention provides media capable of effecting viral inactivation of biological fluids. Viral inactivation means killing, inactivating, or otherwise rendering non-pathogenic viruses and viral elements, particularly non-lipid-enveloped viruses and prions. The media of the present invention are more highly iodinated than previously available media, and effect greater inactivation in larger scale processes than those previously available.

The present invention includes methods for disinfecting biological fluids by contacting those fluids with the iodinated media of the present invention. Such media or matrix materials afford high surface-area contact with the biological fluid; and such contact can be effected through conventional processes such as column, bed, batch, or filter press/cartridge processes. The present invention thus avails methods for treating biological fluids to inactivate viruses, viral-elements, bacteria, microorganisms, and other pathogens while avoiding concomitant destruction of valuable proteins such as clotting factors and immunoglobulins.

A variety of chromatographic methods and matrix materials are useful in the present invention. The matrix material might be an organic or inorganic compound, a synthetic resin, a polyhydroxylic material, or other suitable insoluble carrier or support material. Such polyhydroxylic materials include starch; polysaccharides such as dextran, dextrin, cellulose, and agarose; polyvinyl alcohol, polyvinyl acetal; and the like. Also useful are matrices based on synthetic resins such as polyacrylamide, methacrylate, azlactone, styrene divinyl benzene copolymers; as well as ceramic- or silica-based materials such as controlled-pore glass; and further include solid beads made of plastic material such as polyethylene, polypropylene, polystyrene and the like.

Polyhydroxylic matrix materials, such as polysaccharides, and synthetic polymers such as polyacrylamide, and mixed polymers thereof, are preferred. Such matrix materials derivatized with cationic functional groups are especially preferred. Accordingly, methods and media derived from ion exchange chromatography are especially preferred.

A wide variety of chromatographic matrices or carrier materials, both charged and uncharged, will take up iodine and, when iodinated, are suitable for disinfecting biological fluids in accordance with the present invention. By use of the phrase "suitable for disinfection of biological fluids" is meant that such materials render non-pathogenic a variety of hardy pathogens, e.g., non-lipid enveloped viruses, without degrading or denaturing labile proteins within said fluid.

Matrix materials, generally, are significant in processes such as these in that they are responsible for imparting the physical properties of the media such as mechanical strength, flow characteristics, behavior toward biological substances, and to some extent, capacity. The matrix material might be porous or nonporous; it might be in bead form or otherwise particulate.

Methods and materials conventionally employed in, e.g., size exclusion or gel filtration chromatography can be effectively employed in the present invention. A variety of suitable matrices are commercially available (e.g., crosslinked polyacrylamide, cross-linked glucose polymer (dextrans), cross-linked agarose, and mixed polymers thereof). More specifically, matrices useful in the present invention include underivatized and derivatized forms of cross-linked dextrans, e.g., SEPHADEX® G-10, G-25, G-50, or G-75 (Pharmacia Biotech AB), PDX (Polydex Biologicals, Ltd.); celluloses; cross-linked agarose, e.g. SEPHAROSE CL2B, CL4B, CL6B, 4 FAST FLOW, 6 FAST FLOW, or BIG BEADS (Pharmacia Biotech AB); BIOGEL® A (BioRad) or agarose-acrylamide mixtures. e.g., SEPHACRYL® S-100, S-200, S-300 or S-400 (Pharmacia Biotech AB); styrene/divinylbenzene copolymerized resins, e.g., POROS® (PerSeptive Biosystems), Bio-Rex® 5 (BioRad), AG® 1, AG® 2 or MP-1 (BioRad); acrylics, e.g., AG®4-X4 (BioRad); polyamine, e.g., AG® 3-X4 (BioRad); azlactone (EMPHAZE™ (3M); hydrophobic resins for hydrophobic interaction chromatography (HIC), e.g., C2 BIOGEL® (BioRad), octyl agarose 4XL (Affinity Chromatography Limited (ACL)); polystyrene beads or polystyrene latex particles; combinations and copolymers thereof, and other suitable matrix materials.

Matrices used in gel filtration chromatography are often fabricated in the form of beads having pores of a specified size. The beads admit or exclude solutes based upon pore size. Smaller solutes penetrate into the beads, and their progress through the column is retarded; while larger molecules, e.g., proteins, are excluded from the interior of the bead and flow through the column more rapidly.

Both pore size and rigidity of the insoluble matrix are determined by the degree of cross-linking and concentration of the polymeric matrix. As the matrix is more highly cross-linked, it is increasingly rigid and excludes ever smaller solutes. Consequently, as the degree of cross-linking increases, so too does the flow rate.

The polymerized, porous, cross-linked dextrans (glucose polymers) known as SEPHADEX® (Pharmacia Biotech AB) are preferred. SEPHADEX matrices are categorized, among other things, based upon the degree of cross-linking of the underlying matrix. SEPHADEX with a "25" or "50" classification excludes most of the significant blood proteins thereby reducing or minimizing residence or dwell time of those proteins. Low residence time, in turn, minimizes the prospects that such proteins will be over-iodinated and consequently denatured. Accordingly, those and similarly structured matrices are preferred.

Especially preferred matrices are those in which the cross-linked polymer matrix has been derivatized with functional groups to impart ion exchange capabilities to the resin. Ion exchange resins appear to be more effective as iodine carriers than unmodified resins. This enhanced carrier capability might be due to the greater ability of the ion exchanging functional group to bind iodide ions; and a locally high concentration of iodide ions might allow for greater binding of iodine, (just as iodine is more soluble in Lugol's solution, which consists of iodine plus iodide).

Ion exchange chromatography is a method of separating molecules based upon electrostatic charge. The method exploits the phenomena involving the formation of electrostatic linkages between the insoluble matrix and the products to be separated. Matrices can be made of organic materials, e.g., polystyrene, methacrylate polymers, acrylamide, agarose, dextran, azlactone, cellulose; or any suitable inorganic material, e.g., ceramics, silica, or other glasses, or any combination of those materials.

Such matrices are derivatized to possess an attached functional group. The functional groups are charged with a buffer of suitable pH. The compounds to be separated are likewise charged by adjusting the mixture to a designated pH before being loaded, e.g., onto a column.

Ion exchange is particularly useful in separating molecules of similar size and structure, e.g., proteins. See, e.g., Renee R. Alexander, and Joan M. Griffiths, *Basic Biochemical Methods,* p. 36 (2d ed. 1993).

An ion exchange matrix consists of an insoluble matrix to which charged groups have been covalently bound. The charged groups are associated with mobile counter-ions. Those counter-ions can be reversibly exchanged with other ions of the same charge without altering the matrix.

The presence of charged functional groups is a fundamental property of an ion exchange resin. The functional group determines the type and strength of the ion exchanger; and the density and availability of groups on the matrix determines capacity. Ion exchange matrices are derivatized with functional groups that are either anionic (negatively charged) or cationic (positively charged); and are termed cation- or anion-exchangers, respectively.

Suitable cationic functional groups (anion exchangers) include aminoethyl (AE-derivatized matrices); diethylaminoethyl (DEAE-derivatized matrices); dimethylaminoethyl (DMAE-derivatized matrices); trimethylaminoethyl (TMAE-derivatized matrices); diethyl-(2-hydroxypropyl) aminoethyl (QAE-derivatized matrices) and similar groups.

Commercially available cationic anion exchange matrices include: DEAE SEPHADEX (Pharmacia Biotech AB or "PB"), DEAE SEPHACEL (PB), DEAE SEPHAROSE FAST FLOW (PB), DEAE SEPHAROSE CL-6B (PB), DEAE SEPHACEL (PB), DEAE POROS (Perseptive BioSystems), QAE CELLEX (BioRad), QAE SEPHADEX (PB), Q SEPHAROSE FAST FLOW (PB), DEAE BIO-GEL A (BioRad), DEAE Cellulose (Whatman, Pierce), AG & Biorex Styrene/Divinyl Benzene Resins (BioRad), Anion exchange Macro-Prep Supports (BioRad), Fractogel® EMD DEAE, TMAC, or DEAE (E. Merck), TOYOPEARL DEAE (TosoHaas), TOYOPEARL-QAE (TosoHaas), Q HyperD® (BioSepra), DEAE TRIS ACRYL® (BioSepra), DEAE SPHEROSIL® (BioSepra).

It is a significant and unexpected advantage of the present invention that positively charged ion exchange resins (e.g., those derivatized with $AE^+$, $DEAE^+$, $QAE^+$, $Q^+$ functional groups) bind iodine rapidly and at high capacity. Anion exchange resins can bind 60% (by weight) or greater iodine and still function effectively in the treatment of biological fluids. Such high capacity iodination affords viral inactivation on a greater scale than that heretofore available; and such scale-up is essential to the commercial practicality of iodine-based viral inactivation processes. Further, iodine uptake of ion exchange resins occurs rapidly; under appropriate conditions, within minutes.

Without wishing to be bound by any theory, we believe that such high capacity iodination is attributable to the fact that the positively charged functional group of the ion exchange resin binds iodine as triiodide anion ($I_3^-$). Accordingly, positively charged anion exchange resins, because of their rapid and high capacity uptake of iodine, are preferred in the materials and methods of the present invention.

Particularly preferred ion exchange resins are DEAE SEPHADEX and QAE SEPHADEX. These and similar ion exchange matrices are preferred as they are typically supplied in dry form and the iodinated matrices are most stable as anhydrous powders. Especially preferred are DEAE SEPHADEX A-25 and A-50, with the former being more preferred because it excludes more proteins, has greater rigidity, and greater flow rate. As a result, the proteins of interest experience reduced dwell time amidst the iodinated media thereby reducing the prospects for denaturation and loss of biological activity.

Alternatively, the use of cation exchange resins is included within the present invention. Common cation exchange resins possess anionic functional groups and include resins derivatized with carboxymethyl moieties (CM-derivatized matrices); phospho moieties; and sulphopropyl (SP-derivatized matrices).

For more information on ion exchange chromatography and the properties of various commercially available media, see, e.g., *Ion Exchange Chromatography, Principles and Methods* (Pharmacia Biotech AB, Uppsala, Sweden, 1995).

When suitable matrices are loaded with iodine, they serve as a controlled source of iodine. Without wishing to be bound by any theory, we believe that in the case of iodine-derivatized ion exchange resins, iodine is released from the ion exchange resin into the aqueous phase, where it contacts the proteins, viruses, and other constituents of the mixture; or it might be that the iodine is directly transferred from the resin to the virus by contact or by passing in proximity to the bound iodine.

Iodination of Media

Various iodination techniques are suitable for iodinating the chromatographic media or insoluble matrix material of the present invention. For example, the chromatographic media can be: (i) mixed dry with elemental iodine at a temperature between 0° C. and 100° C.; (ii) exposed to an iodine vapor-containing environment for a suitable period of time; (iii) mixed in liquid suspension with aqueous solutions containing iodine and iodide (e.g., Lugol's solution); (iv) mixed in suspension with a solution of elemental iodine in alcohol (e.g., ethanol) or other organic solvent or in mixtures of alcohol and water or mixtures of other organic solvent(s) and water; or (v) mixed in solution with an iodinated material that releases iodine into the solution or transfers it to the recipient material, or releases/transfers combinations of iodine and/or iodide and/or other reactive iodine species (e.g., $I_3^-$) in a form that complexes, adsorbs, or otherwise binds with the insoluble matrix material.

The amount of iodine delivered to treated media is a function of a variety of factors. Those factors include: (a) the method of iodination; (b) the chemical nature, particle size, and permeability (pore size) of the media being iodinated; (c) the form and concentration of the iodine species; (d) the size of molecular iodine crystals or particles, (e) the duration and temperature of the treatment; (f) the rate of mixing, agitation or tumbling of the reaction mixture; (g) the nature of the medium for suspending the material being iodinated if applicable; (h) the nature of the medium for dissolving the iodine, if necessary; and (i) the vapor pressure of iodine in the environment.

Preferred methods of iodinating ion exchange resins include sublimation of iodine in the vapor state onto the polymeric resin and physical transfer as by physical contact of the dry resin with dry iodine in vapor or solid state. Since iodine is known to have appreciable vapor pressures at or even below room temperature, sublimation can be achieved by merely exposing the resin to elemental iodine in a closed container. Alternatively, the transfer might be made by combining iodine and matrix material in an aqueous mixture.

The most preferred method of iodination involves mixing dry matrix, especially anion exchange media, with dry iodine. Preferably the dry iodine is in a finely particulate form, such as finely divided flakes or crystals. Iodination can be enhanced by continuous physical mixing of the media and iodine. For example, one can iodinate matrix material by direct contact with elemental iodine in a closed vessel with agitation or tumbling to enhance mixing and promote uniform contact of the materials.

The dry mixing method of iodination affords substantial advantages. The dry mixing method of iodination: i) is rapid, ii) binds iodine in high concentration, and iii) yields an iodinated resin with greater activity and stability.

The rate of iodination is temperature dependent. At lower temperatures the iodination reaction is relatively slow. At higher temperatures iodination occurs more rapidly, however, the absorbing material can become altered or damaged in the process.

Exposure or contact of matrix material and iodine is maintained for a sufficient period of time at temperatures between −80° C. and 120° C. to transfer the desired quantity of iodine to the matrix material. The preferred range of temperatures is between about 4° C. and about 40° C., with the most preferred temperature being ambient room temperature without heating or cooling (generally about 22° C.).

The rate of iodination of matrix material by sublimation or direct physical transfer can also be increased by using finely divided particulate iodine. Generally, as iodine particle size decreases, the rate of iodination increases. Preferably, the elemental iodine is employed in the form of particles in the range of about 0.001–10 mm.

Matrices derivatized with DEAE (e.g., DEAE SEPHADEX) can be iodinated to 60% or greater by weight. The iodine percentage is in reference to the total weight of the iodinated resin (e.g., 100 g of 60% iodinated resin=60 g iodine/40 g resin). The physicochemical characteristics of iodinated resins depend on the concentration of iodine, the mode of iodination, and the temperature at which iodination was performed. For example, when excess iodine (up to 9 times the weight of DEAE SEPHADEX) is incubated for 18 hrs at 4±2° C., the iodinated DEAE SEPHADEX A-25 resin remains as a free flowing powder, but iodination is complete only to about 50% iodine (iodine crystals remain at 60% iodine and above).

At ambient temperature (18 hrs at 22±2° C.), the resin remains as a flowing powder and complete iodination occurs through 60% iodine.

When derivatized at 37° C., the resin remains flowing only up to about 40% iodine; at about 50% iodine and greater, the resin beads agglomerate into large chunks.

When derivatized at or above 50° C., DEAE resin derivatized to 50–60% iodine becomes sticky and difficult to pour, and might appear discolored or charred.

A preferred embodiment of the present invention involves the disinfection of biological fluids through the use of iodinated anion exchange resins in an ion exchange process. Other ion exchange methods and conditions are useful when modified and employed in accordance with the methods of the present invention. Preferred embodiments involve the use of iodinated DEAE-, Q-, QAE-, AE-, DMAE- or TMAE derivatized ion exchange resins. A still more preferred embodiment involves the use of iodinated DEAE SEPHADEX A25.

Matrix materials useful in the present invention are iodinated from about 10% to about 70% iodine (by weight based upon dry weight of the matrix material); preferably from about 20% to about 60%; more preferably from greater than 20% to about 60%; and still more preferably from about 25% to about 50%.

At iodination levels between 10% and 50%, dry ion exchange matrix material (e.g., DEAE SEPHADEX A25) behaves as a flowing powder. At iodination levels above 60%, iodinated matrix materials are typically sticky and difficult to pour dry (Table 4).

The iodinated matrices of the present invention, especially SEPHADEX, are highly storage stable, maintaining potency for many months when kept dry in a sealed container. Dry iodinated ion exchange matrix material should be swelled (hydrated) for a period of from about a few minutes to 24 hours or more prior to use. The material can be hydrated in water, saline, or appropriate buffer solution.

When using the iodinated matrices of the present invention, one should avoid organic buffers such as histidine-based or imidazole-based buffers as these compounds themselves quickly exhaust the supply of iodine. Other organic buffers are weak iodophors and tend to dissolve an excess amount of iodine from the column. With buffers of this type, the column might be prematurely stripped of iodine. When using organic buffers it is advisable to test a small quantity of iodinated matrix material with the intended buffer to see if it strips iodine from the column. If the buffer darkens or the matrix becomes decolorized, the buffer is not suitable.

Both phosphate and acetate buffers have proven useful in the use of the iodinated media of the present invention. A pH range of about 2.5 to 11.5 is acceptable for use in the present invention; although a pH in the range of about 2.5 to about 9.5 will generally be effective. The optimum pH range must be determined for each material depending on the pH stability of the constituent proteins. Since the release of iodine from the matrix is accelerated at alkaline pH, the useful life of the matrix material can be extended and the release of iodine slowed by employing the media of the present invention at slightly acid pH, such as pH in the range of 5.2 to 6.5.

Iodine Capture and Removal

The methods of the present invention include a method for disinfecting a biological fluid comprising: (i) contacting said fluid with a matrix material that has been iodinated at levels from about 10 to about 70% iodine (by weight); and (ii) removing said biological fluid from contact with said insoluble matrix material; and (iii) if necessary, isolating and purifying the proteins of interest.

The methods of the present invention optionally further include capture of free (non-bound) iodine and/or removal of iodine and iodine-associated reaction products (e.g., iodide ions) from the biological fluid.

Iodine capture might be a separate step from that of iodine removal. Capture refers to an immediate often in-line process wherein the protein(s) of interest are separated from free iodine remaining in the biological fluid. Generally, free iodine is extracted from the biological fluid shortly after the fluid contacts the iodinated matrix material. Capture can be accomplished by passing the treated fluid through, e.g., a non-iodinated anion exchange resin, a polyvinyl acetal ("PVA") filter, or other suitable means for achieving high surface area contact with iodine-binding materials.

A preferred method for effecting iodine capture involves two columns in series: the first column is packed with the iodinated matrix material; and the second column is packed with a non-iodinated iodine absorbing material, such as an anion exchange resin. As the biological fluid is passed through the iodinated matrix material, high surface area contact with iodine is achieved; and as the biological fluid proceeds through the second column, high surface area contact with an iodine absorbing material is achieved. Any free or non-bound iodine is thus captured.

Alternatively, capture (or inactivation of residual iodine) is optionally effected by the addition of reducing agents such as ascorbic acid, other reducing sugars, sodium sulfite, glutathione, or other suitable antioxidants following contact of the biological fluid with the iodinated matrix material.

After iodine capture or reduction, the treated product might be exposed to an optional incubation step at 37° C. for about 6–24 hrs to fully inactivate hardy non-enveloped viruses. Incubation can also be carried out at lower temperatures (e.g., 4° C., 22°, 30° C.), but the rate of inactivation of hardy viruses is slower at low temperatures.

Effective capture techniques and/or addition of reducing agents minimize the prospects that proteins will suffer degradation or denaturation by creating a means for further controlling the duration of exposure of the protein to iodine. Thus, proteins within the biological fluid having undergone disinfection in accordance with the present invention retain their natural and biologically active three-dimensional structure. That is, the methods of the present invention afford means for disinfecting protein-containing fluids without denaturing said proteins or otherwise diminishing the biological activity of said proteins.

Iodine removal, on the other hand, refers to the removal of all remaining iodine species and unwanted iodine-associated reaction products following completion of the disinfecting and viral inactivation process. Removal thus refers to a clean-up step that separates the treated protein from reaction products.

Removal can be accomplished by separation processes based upon charge, size, or binding affinity. For example, iodine removal can be effected by contacting the iodine-treated biological fluid with an iodine-binding material to remove iodine from the fluid; alternatively, iodine removal can be effected by isolating or separating the protein(s) of interest from the biological fluid, as by binding the proteins to a cation exchange resin.

Preferred methods for achieving iodine removal include any of the following steps: (i) contacting the iodine-treated biological fluid with a non-iodinated anion exchange resin to remove iodine, iodide and other reaction products from the protein; (ii) contacting the iodine-treated biological fluid with polyvinyl acetal, cross-linked povidone (XLPVP), starch, or other iodine-binding polymer; (iii) diafiltering or ultrafiltering or dialyzing the iodine-treated biological fluid to remove iodine and other reaction products; (iv) gel filtering the iodine-treated biological fluid to separate the low molecular weight iodine and other reaction products from the higher molecular weight protein; (v) contacting the iodine-treated biological fluid with a protein-binding material to bind the protein and permit removal of the iodine from the iodine-treated protein; (vi) contacting the iodine-treated biological fluid with a cation-exchange resin to bind the protein and permit removal of the iodine from the iodine-treated fluid.

Thus, the present invention includes a method comprising (i) contacting a biological fluid with insoluble matrix material iodinated to levels of about 10% to about 70% iodine (by weight); (ii) removing said biological fluid from contact with said insoluble matrix material; (iii) capturing and/or reducing residual free iodine in said biological fluid; (iv) removing remaining iodine and iodine-associated reaction products from said biological fluid; and optionally (v) isolating and/or further purifying the proteins of interest.

Incubation of Iodine-Treated Biological Fluid

Pathogen inactivation continues following the steps of (i) contacting the biological fluid with the iodinated matrix material; (ii) removing said biological fluid from contact with said matrix, and (iii) capture and/or reduction of remaining free iodine. Accordingly, the methods of the present invention optionally include a subsequent incubation step. This achieves maximum inactivation of viruses, bacteria, microorganisms, and other pathogenic species.

A preferred embodiment of the present invention involves incubating the iodine-treated biological fluid at 0° C. to 60° C. for 10 seconds to 60 days following iodine treatment; more preferably, incubating the iodine-treated biological fluid at 20° to 40° C. for 4 to 48 hours; and still more preferably, incubating the iodine-treated biological fluid at 37° C. for 18 to 24 hours.

Thus, the present invention includes a method comprising (i) contacting said fluid with a matrix material iodinated to levels of about 10% to about 70% iodine (by weight); (ii) removing said biological fluid from contact with said insoluble matrix material; (iii) capturing and/or reducing residual free iodine in said biological fluid; (iv) incubating said biological fluid at 0° C. to 60° C. for 10 seconds to 60 days; (v) removing remaining iodine or iodine-associated reaction products from said biological fluid; and (vi) isolating and purifying the protein of interest, if necessary.

Purification and Disinfection of Biological Fluids

A number of proteins and protein-containing solutions can be disinfected with the materials and methods of the present invention. For example, the present invention can be used to disinfect such fluids as: (i) human or animal plasma or sera, before or after fractionation; (ii) lymphatic fluids; (iii) milk, including transgenic milk; (iv) urine; (v) semen; (vi) saliva; (vii) cell culture supernatants and other fluids derived from the production of recombinant proteins; (viii) reaction products derived from vaccine production; and (ix) plant extracts. Biological fluids of particular interest are those containing albumin; protease inhibitors; clotting factors such as Fibrinogen, Factor VII, Factor VIII, and Factor IX; protein C; and immunoglobulins, particularly IgG, including hyperimmune Igs and monoclonal antibodies.

The methods of the present invention are, in some instances, improved by stabilizing the protein or proteins of interest by adding conventional protein stabilizing additives or preservatives to the biological fluid. Those additives include: metal ions or salts such as calcium, magnesium, and manganese; heparin; ethylene diamine tetraacetic acid (EDTA); sucrose and other sugars; cysteine, lysine, glycine, glutathione, and antioxidants.

A preferred embodiment of the present invention involves disinfecting immunoglobulin solutions, particularly immunoglobulin G solutions (IgG), e.g., Immune Serum Globulin, Immune Globulin, intravenous immunoglobulin, Hyperimmune Globulins. More particularly, the methods of the present invention include means for disinfecting immunoglobulin-containing solutions by contacting those solutions with iodinated DEAE (I-DEAE), QAE (I-QAE), TMAE (I-TMAE), or AE (I-AE) derivatized ion exchange matrices, e.g., by passing them through a packed bed of hydrated iodinated DEAE-SEPHADEX A-25.

In accordance with the present invention, immunoglobulin-containing solutions are disinfected by passage through a bed of hydrated iodinated DEAE-SEPHADEX in a solution of ionic strength of 0 to 1.0 at a pH of 2.5 to 9.5. As used herein, ionic strength ($\mu$) is defined as one-half the sum of the square of the charge (Z) multiplied by the molar concentration (m) for each ion of a salt in solution $$\mu = \frac{\sum mZ^2}{2}$$

Another preferred embodiment involves treating immunoglobulin solutions by passing them through a packed bed of hydrated iodinated DEAE-SEPHADEX A-25 in a solution of ionic strength 0 to 0.01 at pH of 5.2 to 6.5. A still more preferred embodiment is treating immunoglobulin solutions by passing them through a packed bed of hydrated iodinated DEAE-SEPHADEX in a solution of ionic strength 0 to 0.001 at pH 5.5 (±0.2) The preferred temperature for treating immunoglobulin solutions with iodinated DEAE-SEPHADEX is 0° C. to 60° C. A more preferred temperature for treating immunoglobulin solutions with iodinated DEAE-SEPHADEX is 4° C. to 37° C. The most preferred temperature for treating immunoglobulin solutions with iodinated DEAE-SEPHADEX is 10 to 30° C.

EXAMPLES

Use of Iodinated Material

Example 1

Viral Inactivation

Six grams of iodinated DEAE SEPHADEX A-25 (I-DEAE) (40% iodine) was swelled in approximately 30 ml of water for 30–60 min. and loaded into a 1.6 cm-diameter chromatographic column. Immunoglobulin suitable for intravenous administration ("IVIG" (Baxter)), prepared as a ten percent liquid, was adjusted to pH 4.8 with 1N HCl. The pH adjusted IVIG was dialyzed extensively against water at 4° C.; and the temperature was raised to ambient temperature.

Porcine parvovirus (PPV) was dialyzed against water to lower the ionic strength. The dialyzed PPV preparation was added to IGIV at a ratio of 1:200. The starting solution was 5% protein and pH 4.26 at 20° C. The mixture was passed over the I-DEAE resin at 10 ml/min. Fractions of 2 ml were collected every 250 ml of effluent for a total of 3L of effluent. Samples were tested for PPV inactivation immediately and after incubation at 37° C. for 18 hr.

Control samples were not passed over the column but were assayed for PPV immediately and after 18 hr. at 37° C.; incubation of controls resulted in a reduction of 0.7 logs of PPV infectivity as compared to unincubated samples. Fewer than 2 logs of PPV were inactivated in iodine-treated samples assayed immediately after collection. Inactivation exceeded the limit of the assay (greater than 4.73 logs) after incubation at 37° C. for 18 hr in all samples of column effluent. The capacity of the column was not exceeded as determined by the color of the resin bed; approximately 30% of the iodine remained in the resin following passage of 3L of a 5% solution.

Example 2

Profile of Iodine Release from Column

IVIG, 10% w/v, was adjusted to pH 4.9 with 1N HCl and dialyzed extensively against water and adjusted to pH 5.52. The mixture (2.8L of 5.8% protein) was passed through a 6 g I-DEAE SEPHADEX column (40% iodine) as in Example 1, at 10.6 ml/min. at 22.5° C. Samples were collected every 25, 50, or 100 ml and analyzed immediately for iodide and iodine with an iodide electrode. The iodine concentration was high (approximately 350 ppm) in the first 25 mL fraction and decreased quickly with increasing effluent volume, dropping to 100 ppm at 100 ml and remaining below 30 ppm between 250 and 2800 ml. The first effluent fraction was discarded; and remaining effluent was pooled (2800 ml) and assayed for antibody binding activity. Results of antibody binding activity are shown in Table 1.

For both rubeola and CMV (cytomegalo virus) antigens (whose antibodies are commonly found in the general population), the antibody titers were unchanged by the viral inactivation treatment. This indicates that the procedure does not adversely affect the IVIG.

TABLE 1

| Antigen | Starting Antibody Titer | Antibody Titer After Iodine |
|---------|------------------------|-----------------------------|
| Rubeola | 512 | 512 |
| CMV | 512 | 512 |

Example 3
Effect of Incubation Time on Viral Inactivation

Freeze-dried Polygam SD IVIG (Manufactured by Baxter for the American Red Cross) was reconstituted as directed by the manufacturer except that sodium acetate was added to a final concentration of 25 mM. This resulted in a starting material of 150 mM NaCl, 25 mM sodium acetate, pH 5.4, 5% protein. PPV was added at a dilution of 1:100. Two grams of I-DEAE (30% iodine) was hydrated in aqueous 0.9% sodium chloride for 30–60 min and loaded into a 1.6 cm-diameter column. Starting material was passed over this column at a rate of 6 ml/min at a temperature of 24° C. Effluent was collected and pooled beginning at the 85-ml point through the 115-ml point. This pooled material was split into 4 aliquots; to 2 aliquots was added 20 μl of 0.1 M ascorbate/ml sample within 10 minutes of collection. Aliquots, with and without ascorbate, were incubated either at 37° C. or at 24° C. PPV assays were performed at various times for the various incubation conditions. In separate experiments, equine myocarditis virus (EMC), bovine viral diarrhea (BVD) virus, and pseudorabies virus (PRV) viruses were also assayed along with the PPV. All were inactivated to greater than 5 logs reduction in activity. Because PPV was considered to be the most difficult to inactivate, it was used to test the most preferred embodiment.

The reduction of iodine to iodide by the ascorbate was instantaneous. Nonetheless, inactivation of PPV continued for 5 hrs to 20 hrs, depending on the temperature of incubation, even though all free iodine was reduced within 10 min. of collection. Even in the absence of ascorbate, no free iodine was detected after 2 hrs of incubation, at either 24° C. or 37° C. Furthermore, at 37° C., free iodine levels drop to undetectable levels within 30 min incubation. Elevated iodine levels were used in the latter measurements to facilitate measurement of iodine, as opposed to the preferred levels of Example 2.

Example 4
Capture

Three L of IVIG that had been dialyzed against water (4.9% protein, pH 5.5) was pumped at 10 mL/min through a 1.6 cm-diameter chromatography column containing 6 g of I-DEAE SEPHADEX A-25 (40% iodine) at 11 ml/min. Iodide and iodine in the column effluent were measured with an iodide electrode (Orion). Effluent samples were collected at 25 ml, 1500 ml, 2500 ml; aliquots of the final 2500 ml pool (which did not include the first 25 ml sample) and of the untreated starting material were also taken. The samples were incubated for 20 hours at 37° C. The samples were then dialyzed against 0.15 M sodium chloride to allow removal of non-bound iodine, and against water to remove salts. The results of the corresponding proton induced X-ray emission (PIXE) analysis are shown in Table 2.

TABLE 2

| | PIXE analysis of incubated, dialyzed samples | | | |
|---|---|---|---|---|
| Sample | Iodine ppm in column effluent | IgG % | Iodine (ug/ml) | mol I/mol IgG |
| Untreated IgG | — | 3.9 | 0.0 | 0.0 |
| 25 ml effluent | 349 | 4.7 | 133.7 | 3.47 |
| 1500 ml effluent | 46 | 4.3 | 6.4 | 0.18 |
| 2500 ml effluent | 41 | 5.2 | 9.0 | 0.21 |
| 2500 ml pool | 58 | 4.6 | 13.9 | 0.37 |

The first 25 mL volumes through the column had iodine content of 349 ppm, while later samples had lower levels. After incubation and dialysis, the level of bound iodine was 3.47 mol I per mol IgG in the first 25 mL effluent, and 0.18 to 0.21 for later samples. The level for the entire pool was 0.37 mol I per mol IgG. The higher values for iodine content in table 2 were probably due to the inclusion in these pools of the first effluent fractions containing the highest iodine content.

Another experiment, identical to that described above, but with the column run at lower temperature (4–12° C.) gave results indistinguishable from those shown in Table 2. Iodine content by PIXE analysis was 3.48, 0.25, 0.51 and 0.38 mol I per mol IgG for the 25 ml, 1500 ml, 2500 ml samples and the 2500 ml pool.

Example 5
Capture of Iodine with DEAE Sephadex A-25

One liter of IVIG (4.7% protein) was dialyzed against water and acidified to pH 5.5. The sample was then passed through a 1 cm diameter chromatography column of I-DEAE SEPHADEX A-25 (40% Iodine) at a rate of 4 ml/mn. The column outlet was connected directly to the inlet of a 1 cm diameter chromatography column of non-iodinated DEAE SEPHADEX A-25. Effluent samples were collected and iodide and iodine were measured with an iodide electrode (Orion). The iodide content plateaued at 4 ppm and then slowly increased to 14.3 ppm. Iodide content was initially 20–27 ppm, and then decreased to 10–14 ppm. These values are significantly lower than those measured without a DEAE SEPHADEX A-25 capture column. Under non-capture conditions the iodine level plateaued near 50 ppm, and the iodide reached levels near 400 ppm (not shown).

Example 6
PPV inactivation after Capture.

One liter of IVIG was dialyzed against water and adjusted to pH 5.5. PPV (1 mL of stock virus, titer 9.1 $\log_{10}$) was spiked into the dialyzed material. The material was passed through a 1.0 cm diameter chromatography column containing 2 g of I-DEAE SEPHADEX A-25 (40% iodine) at a flow rate of 4 ml/min. The effluent was passed directly into a 1.0 cm diameter column containing 2.0 g of non-iodinated DEAE SEPHADEX A-25, which had been swelled and washed in water. Samples of effluent from the second column were taken at 100 ml intervals, and were assayed for virus titer after incubation for 24 hours at 37° C. Virus titers in all samples dropped to below the detection limit of the assay ($\leq 1.7$ logs). The final 1000 ml pool of effluent was also collected; and aliquots (with or without 10 or 20 mM sodium ascorbate additions were incubated for 0, 2, 4, 6 and 24 hours at 37° C. and assayed for viral inactivation. Viral inactivation is shown in Table 3. Hold controls (PPV-spiked starting material which was held at room temperature during the column run, and was incubated at 37° C. along with the iodine-treated samples) lost less than 2 logs of viral infectivity during the experiment.

TABLE 3

| Hours incubated at 37° C. | Log PPV Inactivation | | |
|---|---|---|---|
| | No Ascorbate | 10 mM Ascorbate | 20 mM Ascorbate |
| 0 | 0 | 0 | 0 |
| 2 | 0.3 | 1.2 | 2.1 |
| 4 | 1.5 | 3.1 | 3.5 |
| 6 | 2.8 | 3.3 | 3.5 |
| 24 | ≧3.8 | ≧3.8 | ≧4.1 |

Example 7
Kinetics of PPV Inactivation

The experimental conditions similar to Example 1 were employed, except that the PPV was undialyzed and IVIG pH was 5.5. A column was prepared as in Example 1 and run at 4.5° C. The aliquots of the total pooled effluent (3L) were incubated at 4° C., 22° C., and 37° C. for 1, 2, 4, and 22 hrs prior to viral assays. At 4° C., viral inactivation was minimal. Incubation at 22° C. resulted in an inactivation of 2.4 logs at 22 hrs. Incubation at 37° C. was the most effective, with viral inactivation of 2.6 logs in 4 hrs and a ≧4.75 logs in 22 hours.

Iodine Content of Treated Proteins

The tests described above have shown that methods for treating biological fluids with iodinated media are effective in destroying or inactivating various durable pathogens including non-lipid viruses, bacteria, microorganisms, and other pathogenic species. However, in evaluating the safety of treating patients with iodine disinfected proteins, it is important to know to whether iodine treatment has altered the proteins. One test is that of protein function, i.e., determine if the treated proteins (e.g., IgG) function properly. This is a sensitive test for protein denaturation. Another test is to quantitatively analyze the protein for iodine; if the iodine count is low (i.e., one atom or fewer per protein molecule), it is likely that the protein damage is minimal or insubstantial. That measurement can be made reliably by Proton Induced X-ray Emission (PIXE).

Example 8(a)

One liter of reconstituted intravenous immunoglobulin (IVIG), 2.8% w/v, which had been acidified to pH 5.5 and dialyzed against water, was passed through a 1.6 cm diameter column containing 2 g of I-DEAE SEPHADEX A-25 (40% iodine) (prepared as described above), at a flow rate of 10 ml/min (300 cm/hr, total passage time 100 min). The pool of treated IVIG was incubated at 37° C. overnight (19 hours).

A sample of the pool of treated IVIG was dialyzed extensively against 0.15 M sodium chloride to pH 4 to remove non-bound iodine. After dialysis the IVIG, 2.8% w/v (Sample #1), was sent to PIXE Analytical Laboratories, Inc. (Tallahassee, Fla.) for elemental analysis by PIXE.

A sample of the dialysis fluid (acidified saline) from the outside of the dialysis bag was also sent for PIXE analysis (Sample #1 [dialyzed]).

Example 8(b)

In a separate experiment, 3 L of liquid IVIG (5.8% w/v) that had been acidified and dialyzed against water, was pumped through a 1.6 cm column containing 6 g of I-DEAE (40% iodine) SEPHADEX A-25 at 10 ml/min. The pool of treated IVIG was incubated at 37° C. for about 18 hours and then dialyzed against acidified saline to remove non-bound iodine, and then against water to remove salt. The resulting dialyzed sample, 3.96% w/v protein, was sent for PIXE analysis (Sample #2).

Example 8(c)

In a third experiment, 3 L of reconstituted dried IVIG (3.1% w/v) that had been acidified and dialyzed against water, was passed through a 1.6 cm column containing 6 g of I-DEAE (40% iodine) SEPHADEX A-25 at 10 ml/min. The column effluent was then passed through a second 1.6 cm column, connected in series, containing 5 Merocel 150 pads (polyvinyl alcohol acetal, (Merocel Corporation, Mystic, Conn.)) to capture/recycle iodine. The pool of treated IVIG was incubated and dialyzed as described above, and a sample, 1.85% w/v protein, was sent for PIXE analysis (Sample #3).

Results of the PIXE analysis are presented in Table 4:

TABLE 4

| Sample | Iodine (μg/ml) | mol I/mol IgG |
|---|---|---|
| Sample #1 IVIG | 12.4 | 0.54 |
| Dialysis fluid | <1.5 | — |
| Sample #2 IVIG | 30.9 | 0.95 |
| Sample #3 IVIG | 13.3 | 0.88 |

A small amount of iodine (0.54 mol iodine /mol IgG) was bound to IgG after 1 L of IVIG was passed through 2 g of I-DEAE SEPHADEX A-25 (40% iodine) and dialyzed against 0.15M acidified saline solution (Example 8a). No iodine was detected in the dialysis fluid.

At larger scale (3 L of IVIG through 6 g of resin), the amount of iodine bound was 0.95 mol I/mol IgG (Example 8b). That higher level of iodination of the protein probably resulted from higher concentrations of iodine leached from the resin and/or longer residence time in the column.

When the effluent from a 6 g column was pumped through five Merocel pads to capture and/or recycle released iodine (Example 8c), the level of iodination was 0.88 mol I/mol IgG. Use of the pads decreased protein derivatization slightly. Larger numbers of pads would be expected to further decrease protein derivatization.

Immunoglobulin Stability Following Iodine Treatment

The results presented above show that the iodine disinfecting treatment of the present invention contributes less than one atom of iodine per molecule of IgG, suggesting that any damage or denaturation is minimal or insubstantial. However, it is possible that even such slight changes adversely affect the long-term stability of the material. Since IVIG is routinely stored for a considerable period of time before being used to treat patients, tests were undertaken to evaluate both long-term stability and the material's tendency toward aggregation.

IgG activates the complement cascade in vivo. Activation occurs in response to antigen binding, i.e., where multiple antibodies are in close proximity on the surface of the antigen. When in such proximity, complement components bind to opposed Fc regions of IgGs. Polymeric IgG is an aberrant species that can activate the complement cascade in the absence of antigen with potentially serious, even fatal, consequences. Accordingly, the presence of polymeric IgG, and likewise the formation of IgG polymers, is to be studiously avoided, particularly in formulations and fluids for intravenous administration. Anticomplementary activity (ACA) titer is a measure of the biological effect of IgG polymers, and is used, along with HPLC to measure polymer content.

Example 9

The iodine treated material from the 1 L experiment (Sample # 1, above) was used. For controls, dialyzed IVIG was acidified to a pH equal to the Iodine-treated 1 L pool. The 1 L pool and control were sterile filtered and dispensed aseptically into sterile screw-capped 50 ml tubes, which were then stored at: (i) −70° C., (ii) room temperature (RT); and (iii) 37° C.

Tubes were removed after 3 weeks and 6 weeks of incubation and samples analyzed by HPLC to quantitate monomer, dimer and polymer. Little or no increase was observed in polymer up to 6 weeks at all three temperatures; all samples had less polymer than freshly reconstituted IVIG, which contained 0.6% polymer. Dimer content of the treated materials ranged from 0% to 3.8%, and monomer content was over 95.8%.

Samples removed after 6 weeks were assayed for anti-complementary activity (ACA titer). No anticomplementary activity was detected in these samples, in contrast to a detectable level of activity of freshly reconstituted IVIG (43 CH50 units/gram).

Table 5 illustrates that the treatment of IgG by the methods of the present invention does not result in the formation of polymeric IgG. Inappropriate complement activation, as determined by the ACA assay, is undetectable for iodine-treated IVIG. Freshly reconstituted, freeze-dried IVIG, prior to inactivation procedures showed a higher degree of polymerization and a measurable ACA titer as compared to the same material after iodine treatment; indicating that the viral inactivation procedure of the present invention does not promote, and might retard, IgG polymer formation and inappropriate complement activation.

amount of dry elemental iodine is introduced into the container and the container is sealed. The container is placed in an area of controlled temperature. Iodination will proceed either with or without mixing. If mixing is to be used, the sealed container is placed on a mixer, e.g., a FERRIS WHEEL mixer, that rotates the container (preferably end over end).

Other methods can also be used, but require the use of hydrated resin.

Example 10

Loading Matrix Materials from Lugol's Solution

One mL of Lugol's Solution (10% w/v sodium iodide and 5% w/v iodine dissolved in water, "LS") was passed through 1 mL packed beds of saline-washed resins (Q- and DEAE SEPHAROSE FAST FLOW, SEPHAROSE 4B, CM SEPHAROSE 50, and SEPHADEX A25). Each resin was washed with 9 mL of saline, which was collected together with the LS flow-through. Each was then washed with 10 mL saline followed by 10 mL of 4% bovine serum albumin (BSA) in saline. The pools were assayed for iodine/iodide content. Iodine was successfully bound to resin by this method of loading, and the treated resin delivered iodine into saline and/or BSA protein solution.

Example 11

Loading Matrix Materials in 20% Ethanol

Two resins (DEAE-SEPHAROSE FAST FLOW and Q-SEPHAROSE FAST FLOW) were each suspended in 20% ethanol at room temperature (22° C.). Equal volumes of Lugol's Solution and resin/ethanol suspension were mixed and the resins were allowed to settle for 10 minutes. The supernatant was removed and the treated resins were washed several times with saline. Two mL of each resin was packed into a chromatographic column and washed extensively with saline, followed by 4% BSA in saline, and finally saline alone. Iodine and iodide were measured in effluent fractions. Both resins bound iodine by this method, and the amount removed by the protein solution was greater for DEAE than for Q SEPHAROSE FAST FLOW.

TABLE 5

| | | HPLC | | | |
|---|---|---|---|---|---|
| Sample | | Polymer % | Dimer % | Monomer % | ACA Titer (CH50/gram) |
| Freshly Reconstituted IVIG | | 0.6 | 13.3 | 86.2 | 43 |
| Control IVIG, Dialyzed and pH-Adjusted* | Freshly prepared | 0.3 | 0.0 | 99.7 | NA |
| | Stored −70° C. | 0.2 | 2.8 | 96.9 | Undetectable |
| | Inc 3 weeks at RT | 0.3 | 3.5 | 96.2 | NA |
| | Inc 3 weeks at 37° C. | 0.3 | 2.6 | 97.1 | NA |
| | Inc 6 weeks at RT | 0.3 | 3.6 | 96.1 | Undetectable |
| | Inc 6 weeks at 37° C. | 0.1 | 2.0 | 97.9 | Undetectable |
| 1 L Pool of $I_2$-Treated IVIG | Freshly Prepared | 0.2 | 0.0 | 99.8 | NA |
| | Stored −70° C. | 0.3 | 0.0 | 99.7 | Undetectable |
| | Inc 3 wweks at RT | 0.3 | 3.4 | 96.3 | NA |
| | Inc 3 weeks at 37° C. | 0.3 | 2.8 | 96.9 | NA |
| | Inc 6 weeks at RT Inc 6 | 0.3 | 3.8 | 95.8 | Undetectable |
| | weeks at 37° C. | 0.5 | 2.7 | 96.8 | Undetectable |

NA = Not Assayed
*pH 5.5 before the I-DEAE column; pH drops to ~4.5 following passage through the column.

Loading Matrix Materials with Iodine

One method for the successful iodination of an ion exchange matrix, e.g., SEPHADEX anion exchange resin, involves a sublimation process.

A weighed amount of dry SEPHADEX anion exchanger is placed into a container and sealed air-tight. A weighed Example 12

Iodine Binding by Sublimation

One gram portions of seven Pharmacia resins, one Bio-Rad resin, and two known iodine-binding polymers, cross-linked povidone (or "XLPVP") and potato starch, were placed into 15 mL polypropylene tubes together with 100 mg of finely ground iodine powder. The tubes were incubated for 4 days at 55° C. on a slowly turning rotator. Only QAE-SEPHADEX and DEAE-SEPHADEX became dark brown in color (indicating heavy iodination) and successfully competed with the polypropylene tube for iodine binding (tube color clear), indicating that these anion exchange resins have high affinity for iodine.

About half the iodine crystals had sublimed onto the walls of the empty tube within 3 hours at 55 C., turning the tube a deep red color, and no iodine crystals remained after 4 days. Many small iodine crystals were visible in the SP-SEPHADEX, SEPHADEX G-200 and CM SEPHADEX resins after 4 days.

Resins iodinated by sublimation were washed with saline and 4% bovine serum albumin (BSA) in saline, and the released iodine/iodide were measured. Although QAE-SEPHADEX A-50, DEAE-SEPHADEX A-50, XLPVP, and starch bound substantial portions of iodine, flow rates with these materials were too slow to be practical in column mode. Washing with saline alone removed all iodine from SP SEPHADEX, CM SEPHADEX, SEPHADEX G-75, SEPHADEX G-200 and BIO-GEL P-100. To be useful, these resins would need to be used under other conditions (e.g., low ionic strength, low pH, low temperature). BSA/saline gradually removed iodine from SEPHADEX G-10. This iodinated resin might be applicable for treating protein solutions.

Example 13
Comparison of Matrix Materials (Sublimation)

Finely ground iodine was added to 1 gram portions of QEA SEPHADEX A-25 and A-50 and DEAE SEPHADEX A-25 and A-50 in 50 mL polypropylene tubes. Iodine levels were 10%, 15%., 20%, 25%, 30%, 40% and 50% of the total weight of resin plus iodine. The samples were incubated at 45° C. for two days. Tube color and resin color were comparative measures of iodine affinity for the resins. Each iodinated resin (50 mg) was incubated with BSA in phosphate-buffered saline (PBS) and leaching was assessed. Based on tube color and iodine release into BSA/PBS, the relative affinities of these resins for iodine are: DEAE SEPHADEX A-50>QAE SEPHADEX A-50>DEAE SEPHADEX A-25>QAE SEPHADEX A-25.

Example 14
Comparison with Transfer from PVP-I

Iodine was dissolved to saturation (2% w/v) in 70% ethanol. Polyvinyl pyrollidone iodine (PVP-I) was dissolved to saturation in water (6.7% w/v). Four columns were packed with 5 mL of Q SEPHAROSE FAST FLOW and Q SEPHAROSE BIG BEADS (two columns each resin). Each iodine solution was loaded onto each resin until the entire resin was a uniform brown color. Pools of the flow-through load material were collected and analyzed for iodine concentration ([I]) to determine the iodine breakthrough binding capacity.

Q-SEPHAROSE resins bound 28–29 mg iodine per mL resin from 2% iodine in 70% ethanol; and 50 mg iodine per mL from 6.7% PVP-I/water. Results were indistinguishable for FAST FLOW and BIG BEAD resins.

Example 15
Sublimation Conditions for DEAE SEPHADEX A-25

Samples of DEAE SEPHADEX A-25 resin were weighed (1.9 g, 1.2 g, 1.0 g, 0.8 g, 0.6 g, 0.4 g, 0.2 g) and placed in 15 mL screw-capped polypropylene tubes, along with ground iodine crystals in sufficient weight to bring the total weight to 2.0 g (i.e., 0.1 g., 0.8 g, 1.0 g, 1.2 g, 1.4 g, 1.6 g, and 1.8 g). Iodine concentrations (% by weight) in these mixtures were 5%, 40%, 50%, 60%, 70%, 80%, and 90% w/w, respectively. Three tubes were prepared with each resin/iodine combination. One tube of each was agitated slowly on a rotator at 4° C.; one was incubated at 22° C.; and one at 37° C. with frequent manual rotation. The appearance and physical characteristics of the resins are described in Table 6.

TABLE 6

Physical Characteristics of 5%–90% w/w Iodinated DEAE SEPHADEX A-25 Prepared by Sublimation for 18 hours at 4° C., 22° C. and 37° C.

| Temperature of Incubation | Iodine (% of total wt) | Color of Resin | Physical Character of Resin | Iodine Remains |
|---|---|---|---|---|
| 4° C. | 5 | brown | flowing powder | no |
| | 40 | blue/black | flowing powder | no |
| | 50 | blue/black | flowing powder | no |
| | 60 | blue/black | flowing powder | yes |
| | 70 | blue/black | flowing powder | yes |
| | 80 | blue/black | flowing powder | yes |
| | 90 | blue/black | flowing powder | yes |
| 22° C. | 5 | light brown | flowing powder | no |
| | 40 | blue/black | flowing powder | no |
| | 50 | blue/black | flowing powder | no |
| | 60 | blue/black | flowing powder | no |
| | 70 | blue/black | flowing powder | yes |
| | 80 | blue/black | flowing powder | yes |
| | 90 | blue/black | flowing powder | yes |
| 37° C. | 5 | light brown | flowing powder | no |
| | 40 | blue/black | flowing powder | no |
| | 50 | blue/black | powder + chunks | no |
| | 60 | blue/black | chunks + balls | no |
| | 70 | blue/black | chunks + balls | no |
| | 80 | blue/black | chunks + some balls | yes |
| | 90 | blue/black | chunks | yes |

Those skilled in the art will appreciate that various adaptations, modifications, and further optimization of the invention described herein can be routinely effected without exceeding the scope of the present invention. Therefore, it is to be understood that, the invention can be practiced other than as expressly described herein while remaining within the scope of the appended claims.

What is claimed is:

1. Iodinated media suitable for disinfecting biological fluids comprising a matrix material derivatized to possess a cationic functional group selected from the group consisting of aminoethyl, diethylaminoethyl, and dimethylaminoethyl, said matrix material iodinated to levels from greater than 20% to about 70% iodine (by weight).

2. The iodinated media of claim 1, wherein said matrix material comprises a cross-linked polysaccharide.

3. The iodinated media of claim 2 further comprising a cross-linked acrylic polymer.

4. The iodinated media of claim 2, wherein said matrix material is selected from the group consisting of dextran, agarose, cellulose, and mixtures thereof.

5. The iodinated media of claim 1, wherein the matrix material is fabricated into a porous, particulate structure.

6. The iodinated media of claim 5, wherein the particulate structure is a spherical bead.

7. The iodinated media of claim 1, wherein said matrix material is complexed with about 25% to about 50% iodine (by weight).

8. The iodinated media of claim 1, wherein said matrix material is complexed with about 30 to 40% iodine (by weight).

9. Iodinated media suitable for disinfecting biological fluids comprising a cross-linked polysaccharide anion exchange matrix material iodinated to levels from about 25% to about 60% iodine (by weight).

10. Iodinated media suitable for disinfecting biological fluids comprising a DEAE-derivatized cross-linked dextran matrix material iodinated to levels from about 25% to about 60% iodine (by weight).

11. Iodinated media suitable for disinfecting biological fluids comprising a cross-linked cellulosic anion exchange matrix material iodinated to levels from about 25% to about 60% iodine (by weight).

12. A method for disinfecting a biological fluid comprising contacting said fluid with an iodinated insoluble anion-exchange matrix material to which is complexed greater than 20% to about 70% iodine (by weight).

13. The method of claim 12, wherein said matrix material is iodinated to a concentration of greater than 20% to about 60% iodine (by weight).

14. The method of claim 12, wherein said matrix material is iodinated to a concentration of about 25% to about 50% iodine (by weight).

15. The method of claim 12, further comprising a step of iodine capture following contact of said biological fluid to said iodinated matrix material.

16. The method of claim 15, further comprising a step of incubating the biological fluid following contact of the biological fluid with the iodinated matrix material and subsequent iodine capture.

17. The method of claim 16, further comprising a step of iodine removal to eliminate residual iodine and iodine-associated reaction products.

18. A method for disinfecting a biological fluid comprising:
   a. contacting said fluid with an iodinated matrix material binding about 20% to about 70% iodine (by weight);
   b. removing said biological fluid from contact with said matrix material;
   c. effecting iodine capture;
   d. incubating said biological fluid; and
   e. effecting iodine removal.

19. The method of claim 18, wherein said matrix material is an anion exchange resin.

20. The method of claim 19, wherein said anion exchange resin is iodinated from 20% to about 60% iodine (by weight).

21. The method of claim 19, wherein said anion exchange resin is iodinated from about 25% to about 50% iodine (by weight).

22. The method of claim 19, wherein said contact is effected by passing said biological fluid through a column or filter press or cartridge packed with said iodinated anion exchange resin.

23. The method of claim 19, wherein said contact is effected by a bed or batch-type process.

24. The method of claim 18, wherein said contact is effected at a pH of about 5.0 to about 6.5.

25. The method of claim 24, wherein said contact is effected at a pH of about 5.0 to about 6.0.

26. The method of claim 18, wherein said capture is effected by high surface area contact of said biological fluid with an iodine-binding material selected from the group consisting of an anion exchange resin, polyvinyl acetal, polyvinyl pyrrolidone, and activated carbon.

27. The method of claim 18, wherein said incubation of said biological fluid is carried out over a duration of about 2 to about 48 hours at a temperature of about 30°–40° C.

28. The method of claim 18, wherein said incubation of said biological fluid is carried out over a duration of about 18 to about 24 hours at a temperature of about 37° C.

29. The method of claim 18, wherein said step of iodine removal is effected by: (i) contacting the biological fluid with an anion exchange resin; (ii) contacting the biological fluid with polyvinyl acetal or other iodine-binding polymer; (iii) diafiltering, ultrafiltering, or dialyzing the biological fluid; (iv) gel filtering the biological fluid; (v) contacting the biological fluid with a protein-binding material to selectively bind the protein; (vi) contacting the iodine-treated biological fluid with a cation-exchange resin to selectively bind the protein; or (vii) contacting the iodine-treated biological fluid with ascorbic acid or other antioxidant to reduce elemental iodine to iodide.

30. The method of claim 18, wherein said step of iodine removal is effected by high surface area contact of said biological fluid with a non-iodinated anion exchange resin.

31. The method of claim 18, wherein said iodine removal is effected by diafiltering, ultrafiltering, or dialyzing the biological fluid.

32. The method of claim 18, further comprising the step of assaying a fraction of the biological fluid for the activity of a protein.

33. The method of claim 18, further comprising the step of assaying a fraction of the biological fluid for the presence of a pathogen.

34. A method for disinfecting a biological fluid comprising:
   a. contacting said fluid with an anion exchange resin comprising from 20% to about 60% iodine (by weight);
   b. removing said biological fluid from contact with said matrix material;
   c. incubating said biological fluid for a period of about 4 to about 48 hours at a temperature of about 30° C. to about 40° C.;
   d. effecting iodine removal; and
   e. assaying a fraction of the resulting biological fluid for activity associated with a protein.

35. The method of claim 34, wherein said step of removing said biological fluid from contact with said matrix material is followed by a step of iodine capture.

36. The method of claim 35, wherein said iodine capture is effected by contacting said biological fluid with an anion exchange resin or polyvinyl acetal.

37. The method of claim 34, wherein said anion exchange resin comprises a functional group selected from the group consisting of diethyl aminoethyl, diethyl-(2-hydroxypropyl) aminoethyl, dimethylaminoethyl, and trimethylaminoethyl.

38. The method of claim 34, wherein said biological fluid is adjusted to an ionic strength of from about 0.0 to about 1.0 and a pH of from about 2.5 to about 11.5 prior to contacting said fluid with said iodinated ion exchange resin.

39. The method of claim 34, wherein said biological fluid is adjusted to an ionic strength of from about 0.0 to about 0.01 and a pH of from about 4.0 to about 6.5 prior to contacting said fluid with said iodinated ion exchange resin.

40. The method of claim 34, wherein said biological fluid is adjusted to an ionic strength of from about 0.0 to about 0.001 and to a pH of about 5.5 prior to contacting said fluid with said iodinated ion exchange resin.

41. The method of claim 34, wherein the activity for which a fraction is assayed is activity associated with immunoglobulin.

42. The method of claim 34, wherein the activity for which a fraction is assayed is activity associated with a clotting factor.

43. The method of claim 34, wherein a protein-stabilizing additive is present in said biological fluid during contact with said iodinated ion exchange resin.

44. The method of claim 43, wherein said stabilizing additive is a selected from among the group consisting of: ions or salts of calcium, magnesium, or manganese; heparin; EDTA; sucrose; cysteine, lysine, glycine, glutathione, and antioxidants.

45. The method of claim 43, wherein said additive is a calcium salt.

46. A method for disinfecting a biological fluid comprising:
   a. adjusting said fluid to an ionic strength of from about 0.0 to about 0.1, and a pH of from about 4.0 to about 6.0;
   b. contacting said fluid with an iodinated DEAE-derivatized ion exchange resin to which is complexed about 25% to about 50% iodine (by weight);
   c. removing said biological fluid from contact with said ion exchange resin;
   d. incubating said biological fluid for a period of about 18 to about 24 hours at a temperature of about 37° C.; and
   e. effecting iodine removal.

47. The method of claim 46, wherein said step of removing said biological fluid from contact with said iodinated ion exchange resin is followed by a step of iodine capture effected by contacting said biological fluid with a non-iodinated anion exchange resin or polyvinyl acetal.

48. A method for complexing iodine to ion exchange matrix material to levels greater than 20% iodine (by weight) comprising (i) mixing the dry matrix material with dry elemental iodine at a temperature between 0° C. and 100° C.; (ii) exposing said matrix material to an iodine vapor-containing environment for a suitable period of time; (iii) mixing said matrix material in liquid suspension with aqueous solutions of iodine and iodide; (iv) mixing said matrix material in suspension with a solution of elemental iodine in a water-miscible organic solvent or in aqueous mixtures of water-miscible organic solvents; or (v) mixing said matrix materials in solution with an iodinated material that releases iodine into the solution or transfers it to the recipient material.

49. A method for iodinating anion exchange matrix material to levels greater than 20% iodine (by weight) comprising exposing said matrix material to finely divided elemental iodine in a closed, air-tight vessel.

50. The method of claim 49, wherein said iodination occurs at a temperature between about 4° C. and about 40° C.

51. The method of claim 49, wherein said iodination occurs at about 40° C. to about 25° C.

52. The method of claim 49, wherein said iodination is carried out with agitation of said closed vessel.

* * * * *